United States Patent [19]

Sanders et al.

[11] 4,166,916

[45] Sep. 4, 1979

[54] SUBSTITUTED BICYCLOOCTENEMETHANOLS

[75] Inventors: James M. Sanders, Eatontown; Joaquin F. Vinals, Red Bank; Frederick L. Schmitt, Holmdel, all of N.J.

[73] Assignee: International Flavors & Fragrances Inc., New York, N.Y.

[21] Appl. No.: 913,697

[22] Filed: Jun. 8, 1978

Related U.S. Application Data

[62] Division of Ser. No. 780,685, Mar. 23, 1977, Pat. No. 4,128,729.

[51] Int. Cl.² .................. C07C 35/22; C07F 3/02
[52] U.S. Cl. .................. 568/820; 260/586 G
[58] Field of Search ......................... 568/820

[56] References Cited

U.S. PATENT DOCUMENTS

| | | | |
|---|---|---|---|
| 3,255,254 | 6/1966 | Kauer | 568/820 |
| 3,337,498 | 8/1967 | Hogsed et al. | 568/820 |
| 3,515,740 | 6/1970 | Frampton | 568/820 |
| 3,879,466 | 4/1975 | Light | 568/820 |
| 3,914,332 | 10/1975 | Chappell et al. | 568/820 |
| 4,062,878 | 12/1977 | Pesnelle et al. | 568/820 |
| 4,064,184 | 12/1977 | Light et al. | 568/820 |

OTHER PUBLICATIONS

Bates et al., "J. Org. Chem.", 34:2615 (1969).
"Nippon Kogaku Zasohi", 1971, 92(10), 874–876.

*Primary Examiner*—Norman Morgenstern
*Attorney, Agent, or Firm*—Arthur L. Liberman; Franklin D. Wolffe

[57] ABSTRACT

The use of unsaturated bicyclooctenemethanols to augment or enhance the organoleptic properties of perfumes, tobaccos and perfumed articles and particularly the aroma of perfumes and perfumed articles and the aroma and taste of tobaccos, together with compositions containing such bicyclooctenemethanols and processes for preparing them, said bicyclooctenemethanols having the generic structures:

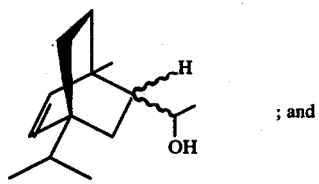

; and

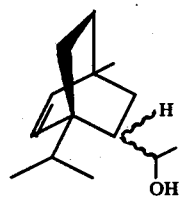

wherein the wavy line represents exo or endo configurations of the ethanol moiety with respect to the carbon-carbon double bond of the bicyclooctene moiety; and intermediates useful in processes for preparing such bicyclooctenemethanols which intermediates have the structures:

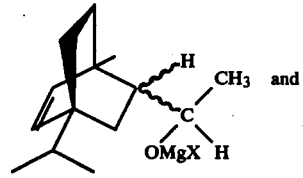

and 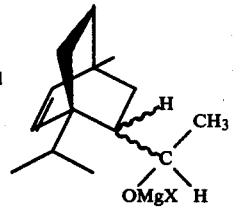

wherein X is a halogen selected from the group consisting of chlorine, bromine and iodine.

3 Claims, 7 Drawing Figures

IR SPECTRUM FROM EXAMPLE II

FIG.5

SUBSTITUTED BICYCLOOCTENEMETHANOLS

This is a divisional of application Ser. No. 780,685, filed Mar. 23, 1977 now U.S. Pat. No. 4,128,729.

BACKGROUND OF THE INVENTION

The present invention relates to certain bicyclooctenemethanol derivatives and the uses thereof in augmenting or enhancing organoleptic properties of consumable materials such as tobacco flavors, perfume and perfumed article aromas, and compositions suited to such uses, and processes for preparing such bicyclooctene derivatives as well as intermediates used in such processes.

There has been considerable work performed relating to substances which can be used to impart (modify, augment or enhance) tobacco flavors and fragrances in perfumery and perfumed articles to (or in) various consumable materials e.g., tobacco, perfumes and perfumed articles. These substances are used to diminish the use of natural materials, some of which may be in short supply and to provide more uniform properties in the finished product.

Sweet, woody, floral aromas with clary sage, violet leaf and orris nuances are desirable in several types of perfume compositions, perfumed articles and colognes.

Sweet, oriental, spicey and woody aromas prior to smoking and on smoking, in the mainstream and in the sidestream, are desirable in tobaccos and in tobacco flavoring compositions.

In the art of perfumery and in the art of tobacco flavoring, bicyclooctene derivatives are known for their properties in augmenting or enhancing aromas and flavors.

Thus, for example, a material having the structure:

(dioxolane-substituted 5-isopropyl-7-methylbicyclo[2.2.2]-oct-7-ene) has been sold by Societe Anonyme Des Establissements Roure Bertrand Fils Et Justin Dupont, 17 Bis Rue Legendre, Paris XXVII$^e$, France under the name "Glycollierol" for use in perfumes. Dragoco, Gerberding & Co., GmbH, Holzminden, Federal Republic of Germany, has sold a material having the structure:

(carbomethoxy-substituted 1,4-dimethyl-bicyclo[2.2.2]oct-5-ene) as a perfume ingredient with a patchouli, vetivert type odor, under the name "Mahogonate".

U.S. Pat. No. 2,957,906 broadly shows acyl- and carboalkoxy-substituted bicyclooctene, among other bicyclic compounds for pesticide and agricultural uses, and U.S. Pat. No. 3,304,167 shows various norbornane(bicyclo[2.2.2]heptane) derivatives, including nitrile derivatives and certain of the materials are said to be herbicidally active.

Danishevsky, et al., Chem. Comm. 1968, 1287, show 1,3,3-trimethyl-6-isobutylbicyclo[2.2.2]octan-2-one and Kealy et al., J. Org. Chem., 26, 987 (1961) demonstrate 1,3-dimethyl-3-ethylbicyclo[2.2.2]octane and the corresponding bicyclooct5-ene. Orahovats et al., Collect. Czech. Chem. Comm., 35(3), 838 (1970) show 2-hydroxy- and 2-oxo-substituted 3-methylbicyclo[2.2.2]oct-5-ene and the corresponding bicyclooctane. Organic Reactions, IV, 66 states that Diels and Alder, Ann. 478, 137 (1937) prepared bicyclo[2.2.2oct-5-ene-8-carboxaldehyde and that 2-isopropyl-5-methylbicyclo-[2.2.2]-oct-5-en-7- and 8-(carboxaldehyde were prepared by Diels and Alder, Ann. 470, 62 (1929).

Morita et al., J. Org. Chem. 30, 533 (1965, show various alkylated 4-alkoxybicyclo-[2.2.2]-octan-2-ones, and Curtin et all, J. Am. Chem. Soc. 81, 622 (1959) show methylated bicyclo[2.2.2]oct-5-en-2-ones. Various other bicyclo[2.2.2]-octane materials and methods for their preparation are demonstrated by Petrov, J. Gen. Chem. U.S.S.R., 11, 809 (1941); Selca et all, Ber. 75, 1379 (1942); Kenyon and Young, J. Chem. Soc. 263 (1941); Alder et al., Ann. 543,1 (1939); Tich et al., Collect. Czech. Chem. Comm. 35(2), 459 (1970); Kraus et al. Ann. 708, 127 (1967); Berson et al., J. Am. Chem. Soc. 80, 5010 (1964); Karanskil et al., Zh. Obshchei Khim. 29, 2976; McDonald et al., J. Org. Chem. 35, 1250 (1970); Curtain et al., J. Am. Chem. Soc. 81, 662 (1959); Conroy et al., J. Am. Chem. Soc. 75, 2530 (1953) and 78, 2290 (1957); Curtain et al., J. Am. Chem. Soc. 79, 3156 (1957); Waring et al., J. Am. Chem. Soc., 86, 1454 (1964); Alder et al., Ber. 90, 1709 (1957); Cookson et al., J. Chem. Soc. 2302 (1956); Kamemato, Chem. Abst. 58, 2391f (1963); and Cimarusti et al., J. Am. Chem. soc. 90, 113 (1968).

German Offenlegungsschrift 2,242,913 shows a tricyclic alcohol, denominated "nordehydro-patchoulol", extracted from patchouli alcohol. Tricyclic compounds have also been prepared by Greuber et al., Helv. Chim. Acta 55, 526 (1972). Various preparative procedures for preparation of tricyclic material are exhibited by Waring et at., J. Am. Chem. Soc. 86, 1454 (1964) and Blum et al., Synthesis No. 4, 195 (1972). Quinones and quinols have been prepared by Chambers et al. J. Chem. Soc. (London) 1804 (1959) and McClure, J. Org. Chem. 28, 69 (1963). Various cyclic derivatives are demonstrated by Alder et al., Ber. 90, 1709 (1957) and Day, Chem. Rev. 53, 167 (1953).

In addition, U.S. Pat. No. 3,914,322 provides for the use of certain alkylated saturated and unsaturated derivatives of bicyclo[2.2.2]octane, as well as certain novel derivatives and processes for preparing them. The compounds for use in altering the organoleptic properties of materials can be represented by the formula:

wherein the dashed lines represented single or double carbon-to-carbon bonds; one of $R_2$ and $R_3$ is hydrogen or alkyl and the other is hydrogen or hydroxy or, taken together, $R_2$ and $R_3$ are carbonyl oxygen; $R_4$ and $R_5$ are alkyl; $R_1$, $R_6$, $R_7$ and $R_8$ are hydrogen or alkyl; and one of $R_9$ and $R_{10}$ is hydrogen, alkyl, cyano, carboalkoxy, or aliphatic acyl and the other is hydrogen, at least five of $R_1$ through $R_{10}$, inclusive, being other than hydrogen.

In general, the Diels-Alder reaction product of 1,3-paramenthadiene with acrolein is disclosed in Nippon Kagaku Zasshi 1971, 92(10), pages 874–6. The genus of compounds disclosed has the structure:

wherein one of $R_1$, $R_2$, $R_3$ and $R_4$ is carboxaldehyde and each of the other of $R_1$, $R_2$, $R_3$ and $R_4$ is hydrogen. However, no utility for these carboxaldehydes is disclosed in the Nippon Kagaku Zasshi reference. Furthermore, no compounds of the prior art that are similar in structure to the compounds of the instant invention are disclosed to have properties even remotely similar to those of the compounds of the instant invention.

THE INVENTION

It has now been discovered that novel solid and liquid perfume compositions, colognes and perfumed articles having sweet, woody, floral aromas with clary-sage, violet leaf and orris undertones as well as novel tobacco and tobacco flavoring compositions having sweet, oriental, spicey, woody and tobacco-like aromas with sweet, tobacco/hay-like nuances in the mainstream and in the sidestream on smoking and prior to smoking, may be provided by the utilization of one or a mixture of the bicyclo [2.2.2]octenemethanol derivatives of our invention having one of the formulae:

-continued

; and wherein the wavy line represents exo or endo configurations of the ethanol moiety with respect to the carbon-carbon double bond of the bicyclooctene moiety of the molecule and wherein, in those representations where wavy lines appear, mixtures are intended to be represented; and wherein in the ethanol moiety a heavy line indicates that the substituent hydroxyl or hydrogen group lies above a plane defined by the two carbon atoms of the ethanol side chain and the site of attachment of the side chain to the bicyclooctene moiety and a dotted line indicates that the substituent hydroxyl or hydrogen groups lies below this plane.

The bicyclooctenemethanol derivatives of our invention are prepared according to a process whereby the compound 1-methyl-4-(2-propenyl)cyclohexene-1 (also referred to herein as "limonene") is isomerized to form 1-methyl-4-isopropyl-1,3-cyclohexadiene (also referred to herein as "alpha-terpinene") and other double bond isomers. The 1-methyl-4-isopropyl-1,3-cyclohexadiene thus formed is separated from the reaction mixture and is then reacted (in admixture without being isolated, or if desired, after isolation) via a Diels-Alder reaction with acrolein thereby forming a mixture of carboxaldehydes. This mixture of carboxaldehydes is then reacted with a methylmagnesium halide thereby forming a mixture of oxymagnesium halide compounds. This mixture of oxymagnesium halide compounds is then hydrolyzed to form the desired products. The reaction sequences are illustrated as follows:

<u>A</u>

<u>B</u>

<u>C</u>

<u>D</u>

-continued

The endo/exo position isomer mixtures may be separated where desired by techniques such as preparative GLC.

Reaction Step A is preferably carried out using an isomerization reagent such as 50% sulfuric acid, phosphoric acid or paratoluene sulfonic acid. The Diels-Alder reaction is preferably carried out at temperatures of between −20° C. up to +100° C. using a Lewis acid catalyst such as stannic chloride, aluminum trichloride, ethyl aluminum dichloride, zinc chloride and zinc bromide. Preferably, in both reaction sequences A and B solvents can be used which are inert to the reaction products and inert to the reactants themselves. Examples of such inert solvents are benzene, toluene, tetrahydrofuran and cyclohexane.

In the reaction of the bicyclooctenecarboxaldehyde with the Grignard reagent (Sequence C), to wit:

it is preferable that the Grignard reagent be methylmagnesium chloride or methylmagnesium bromide. However, methylmagnesium iodide may also be used for this reaction. The solvent for the reaction may be diethyl ether or tetrahydrofuran or a mixture of diethyl ether and tetrahydrofuran taken alone or taken further together with inert hydrocarbons such as benzene, toluene or xylene.

The reaction temperature for this Sequence "C" may vary from 0° C. up to about 100° C. depending upon the particular solvent used. However, it is preferable to use reaction temperatures of 35° C. up to 75° C. and it is most expeditious to use a reaction pressure of atmospheric pressure, although higher or lower pressures may be used without affecting the yield of product.

The mole ratio of CH₃MgX (methyl Grignard reagent) to bicyclooctenecarboxaldehyde may vary from 0.1:1 up to 10:1 with a mole ratio of methylmagnesium halide to bicyclooctenecarboxaldehyde preferably between 1:1 up to about 2:1.

The compounds which are formed as result of this reaction, the oxymagnesium halide compounds represented by the structures:

are novel compounds wherein the wavy lines illustrate an exo and endo configuration of the ethyloxymagnesium halide moiety with respect to the carbon-carbon double bond of the bicyclooctene moiety.

The resulting oxymagnesium halide may be decomposed using such materials as saturated aqueous ammonium chloride solution or dilute aqueous acids such as dilute acetic acid from 0.5 molar up to 10 molar) or dilute sulfuric acid (e.g., from 0.5 molar up to 3 molar) or 0.1 molar up to 1 molar hydrochloric acid.

At the end of the reaction, the product exists as a mixture of isomers set forth by the generic structures:

wherein the wavy lines represent endo and/or exo configurations of the ethanol moiety with respect to carbon-carbon double bonds of the bicyclooctene moiety. The resulting isomeric mixture, if desired, may be separated by such means as preparative GLC separation. This separation could be refined whereby even the diastereoisomer may be separated out yielding the compounds having the generic structures:

-continued

Thus, our invention provides an organoleptically improved smoking tobacco product and additives therefor as well as methods of making the same which overcome specific problems heretofore encountered in which specific desired sweet, oriental, spicey, woody, tobacco-like, and hay tobacco-like flavor and aroma characteristics of natural tobacco (prior to smoking and on smoking; in the mainstream and in the sidestream) are created or enhanced or modified or augmented and may readily be controlled and maintained at the desired uniform level regardless of variations in the tobacco components of the blend.

The invention further provides improved tobacco additives and methods whereby various desired natural aromatic tobacco flavoring characteristics with sweet, oriental, spicey, woody, tobacco-like and hay tobacco-like notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient one or more bicyclo[2.2.2]-octenemethanol derivatives of our invention.

In addition to the bicyclo[2.2.2]octenemethanol derivatives of our invention, other flavoring and aroma additives may be added to the smoking tobacco material or substitute therefor either separately or in mixture with the bicyclo[2.2.2]-octenemethanol derivatives as follows:

I. Synthetic Materials

Beta-ethylcinnamaldehyde;
Eugenol;
Dipentene;
Beta-damascenone (having the structure:

);

Maltol;
Ethyl maltol;
Beta-damascone (having the structure:

);

Delta undecalactone;
Delta decalactone;
Benzaldehyde;
Amyl acetate;
Ethyl butyrate;
Ethyl valerate;
2-Hexenol-1;
2-Methyl-5-isopropyl-1,3-nonadiene-8-one;
2,6-Dimethyl-2,6-undecadiene-10-one;
2-Methyl-5-isopropylacetophenone;
2-Hydroxy-2,5,5,8a-tetramethyl-1-(2-hydroxyethyl)-decahydronatphthalene;
Dodecahydro-3a,6,6,9a-tetramethylnaphtho-(2,1b)-furan;
4-Hydroxyhexanoic acid, gamma lactone; and
Polyisoprenoid hydrocarbons defined in Example V of U.S. Pat. 3,589,372 issued on June 29, 1971.

II. Natural Oils

Celery seed oil;
Coffee extract;
Bergamot oil;
Cocoa extract;
Nutmeg oil; and
Orignaum oil.

An aroma and flavoring concentrate containing one or more of the bicyclo[2.2.2]octenemethanol derivatives of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet, oriental, spicey, woody and tobacco/hay-like notes, we have found that satisfactory results are obtained if the proportion by weight of the sum total of the bicyclo[2.2.-2]octenemethanol derivatives to smoking tobacco material is between 250 ppm and 1,500 ppm (0.025%–0.15%) of the active ingredients to the smoking tobacco material. We have further found that satisfactory results are obtained if the proportion by weight of the sum total of bicyclo[2.2.2]octenemethanol derivatives used to flavoring material is between 2,500 and 15,000 ppm (0.25%–1.5%).

Any convenient method for incorporating the bicyclo[2.2.2]octenemethanol derivatives into the tobacco product may be employed. Thus, one or more of the bicyclo[2.2.2]octenemethanol derivatives taken alone or along with other flavoring additives may be dissolved in a suitable solvent such as ethanol, diethyl ether or other suitable volatile organic solvent and the resulting solution may either be sprayed onto the cured, cased and blended tobacco material or the tobacco material may be dipped into such solution. Under certain circumstances, a solution of one or more of the bicyclo[2.2.2]octenemethanol derivatives taken alone or taken together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated may have one or more of the bicyclo [2.2.2]octenemethanol derivatives in excess of the amounts of concentrations above indicated so that when blended with other tobaccos, the final product will have the percentage within the indicated range.

In accordance with one specific example of our invention, an aged, cured and shredded domestic burley tobacco is sprayed with a 20% ethyl alcohol solution of the reaction product which has the compounds having the generic structures:

wherein the wavy lines represent exo and endo configurations of the ethanol moiety with respect to the carbon-carbon double bond of the bicyclooctene moiety, in an amount to provide a tobacco composition containing 800 ppm by weight of bicyclo[2.2.2]octenemethanol derivatives on a dry basis. Thereafter, the alcohol is removed by evaporation and the tobacco is manufactured into cigarettes by the usual techniques. The cigarette when treated as indicated has a desired and pleasing aroma which is detectable in the main and side streams when the cigarette is smoked. The aroma is described as being sweeter, more oriental, more woody, more tobacco-like and having sweet, woody, oriental and hay tobacco-like notes.

While our invention is particularly useful in the manufacture of smoking tobacco, such as cigarette tobacco, cigar tobacco and pipe tobacco, other tobacco products formed from sheeted tobacco dust or fines may also be used. Likewise, the bicyclo[2.2.2]octenemethanol derivatives of our invention can be incorporated with materials such as filter tip materials, seam paste, packaging materials and the like which are used along with tobacco to form a product adapted for smoking. Furthermore, the bicyclo[2.2.2]octenemethanol derivatives can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

The bicyclo[2.2.2]octenemethanol derivatives and one or more auxiliary perfume ingredients including, for example, other alcohols, aldehydes ketones, nitriles, esters, cyclic esters (lactones), natural essential oils and other synthetic essential oils may be admixed so that the combined odors of the individual components produce a pleasant and desied fragrance, particularly and preferably in rose fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however, the overall sensory effect of the perfume composition will be at least the sum total of the effects of each of the ingredients. Thus, one or more of the bicyclo[2.2.2]octenemethanol derivatives can be used to alter, modify or enhance the aroma characteristics of a perfume composition, for example, by utilizing or moderating the olfactory reaction contributed by another ingredient in the composition.

The amount of bicyclo[2.2.2.]octenemethanol derivatives of our invention which will be effective in perfume compositions as well as in perfumed articles and colognes depends on many factors, including the other ingredients, their amounts and the effects which are desired. It has been found that perfume compsitions containing as little as 0.01% of bicyclo[2.2.2]octenemethanol derivatives or even less (e.g., 0.005%) can be used to impart a sweet, woody, floral aroma with clary-sage, violet leaf and orris undertones to soaps, cosmetics or other products. The amount employed can range up to 70% of the fragrance components and will depend on considerations of cost, nature of the end product, the effect desired on the finished product and the particular fragrance sought.

The bicyclo[2.2.2]octenemethanol derivatives of our invention are useful [taken alone or together with other ingredients in perfume compositions] as (an) olfactory component (s) in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders, such as talcs, dusting powders, face powders and the like. When used as (an) olfactory component(s) as little as 1% of the bicyclo [2.2.2]-octenemethanol derivative(s) will suffice to impart an intense floral note to rose formulations. Generally, no more than 3% of bicyclo[2.2.2]octenemethanol derivatives based on the ultimate end product, is required in the perfume composition.

In addition, the perfume composition or fragrance composition of our invention can contain a vehicle, or carrier for the bicyclo[2.2.2]octenemethanol derivatives. The vehicle can be a liquid such as a non-toxic alcohol, a non-toxic glycol, or the like. The carrier can also be an absorbent solid, such as a gum, e.g., gum arabic, or components for encapsulating the composition (such as gelatin).

It will thus be apparent that the bicyclo[2.2.2]octenemethanol derivatives of our invention can be utilized to alter, modify or enhance sensory properties, particularly organoleptic properties, such as flavor(s) and/or fragrance(s) of a wide variety of consumable materials.

Examples I–III, following, illustrate a method for preparing the bicyclo[2.2.2]octene derivatives of our invention. Examples IV–XIV, following, illustrate the uses of the bicyclo[2.2.2]octene derivatives of our invention for their organoleptic properties.

It will be understood that these Examples are illustrative and the invention is to be considered restricted thereto only as indicated in the appended claims.

All parts and percentages given herein are by weight unless otherwise specified.

EXAMPLE I

ISOMERIZATION OF LIMONENE

Reaction:

A mixture of 6000 g of limonene and 3000 g of 50% wt./wt. sulfuric acid is stirred at reflux (110–116° C.) for approximately 4.5 hours. The mass is cooled to room temperature, the organic layer is separated, and the aqueous layer is extracted with 1000 g of chloroform. The combined organic layer and chloroform extract are washed successively with 10% salt solution, 10% sodium carbonate solution and 10% salt solution.

The chloroform is recovered by distillation at atmospheric pressure through a short column and the stripped crude product is distilled rapidly at 50 mm Hg. In this way 4713 g of material is obtained, b.p. 94°–103° C./50 mm Hg, which contains approximately 40% alpha-terpinene and is suitable for use without further purification.

Figure 1:
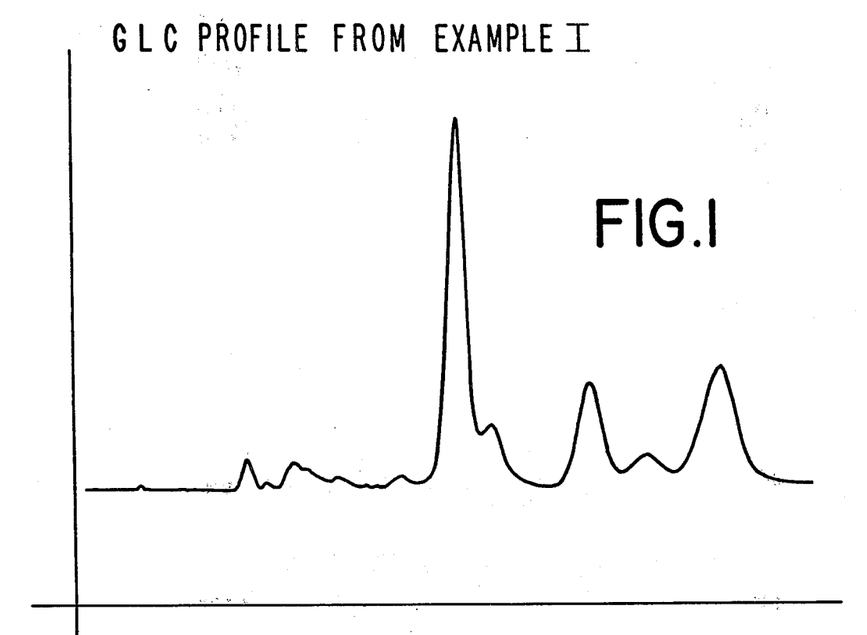
FIG. 1 is the GLC profile of the rearrangement product produced according to Example I.

The GLC profile for the distilled product (conditions: 100° C. isothermal, 10°×⅛", 5% A-20M) is set forth in FIG. 1.

EXAMPLE II

PREPARATION OF 1(and 4)-ISOPROPYL-4-(and 1)-METHYLBICYCLO[2.2.2]OCT-5-ENE-2-CARBOXALDEHYDE Reaction:

A mixture of 470 g of acrolein, 400 g of toluene, and 2380 g of alpha-terpinene (approximately 40%, prepared according to Example I) is added to a mixture of 33 g of anhydrous stannic chloride and 200 g of toluene over a period of 2 hours with external cooling to maintain 5°–10° C. The reaction mass is stirred for an additional 2 hours at 5°–10° C. and then is washed with three 500 g portions of 10% salt solution.

After addition of 50 g of triethanolamine and 3 g of Ionol ® to the washed organic solution, the toluene is removed and the crude product is distilled rapidly through a short column under reduced pressure to give 1567 g of oil, b.p. 72°–156°C./3–4 mm Hg. Redistillation of this material using a 12"×1 ½" Goodloe packed column gives 793 g. of product, b.p. 105°–120° C./3–4 mm Hg, which is shown to be a mixture of isomers having the indicated structures:

wherein the wavy lines represent exo or endo configurations of the carboxaldehyde moiety with respect to the carbon-carbon double bond of the bicyclo[2.2.2]octene moiety.

Figure 2:
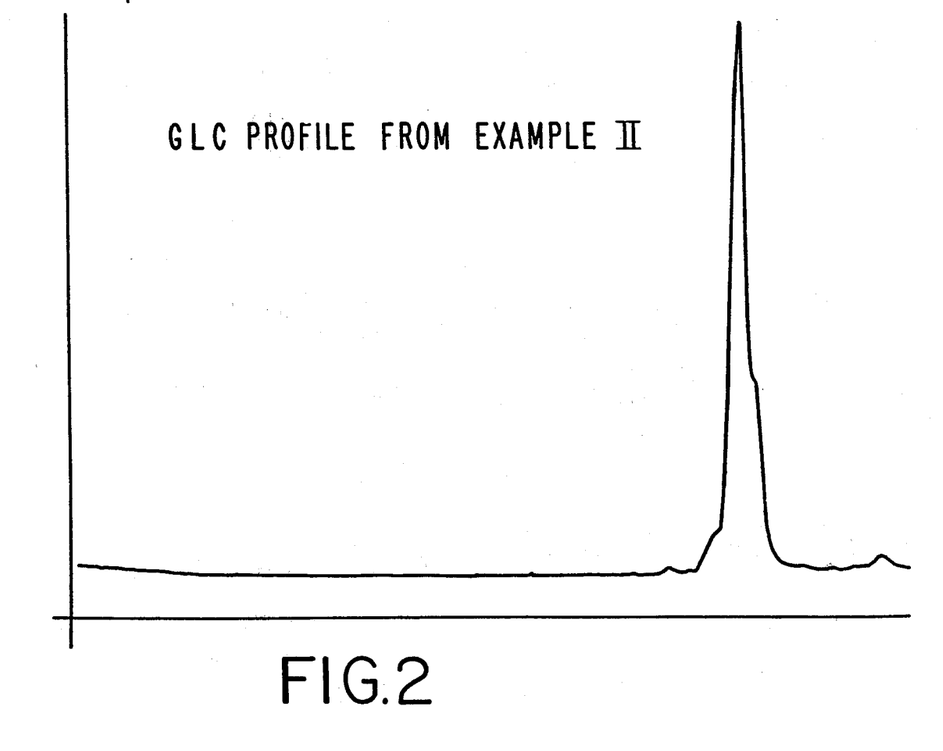
FIG. 2 is the GLC profile of the Diels-Alder reaction product produced according to Example II.

The GLC profile for the reaction product is set forth in FIG. 2 (conditions: 10'×⅛"5% K-20M column, programmed at 100°–200° C. at 10° C. per minute).

Figure 3:
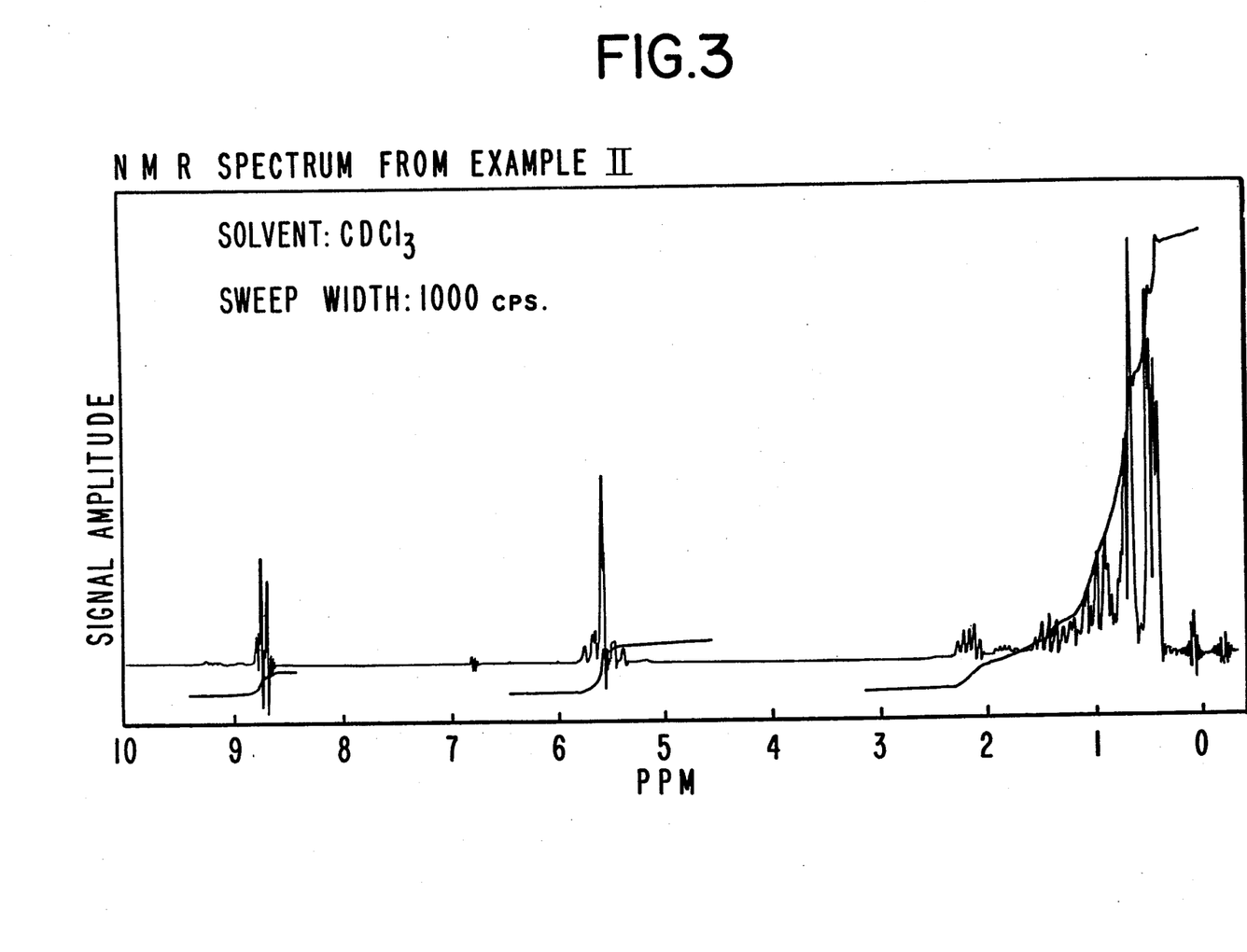
FIG. 3 is the NMR spectrum of the reaction product produced according to Example II.

The NMR spectrum is set forth in FIG. 3.

Figure 4:
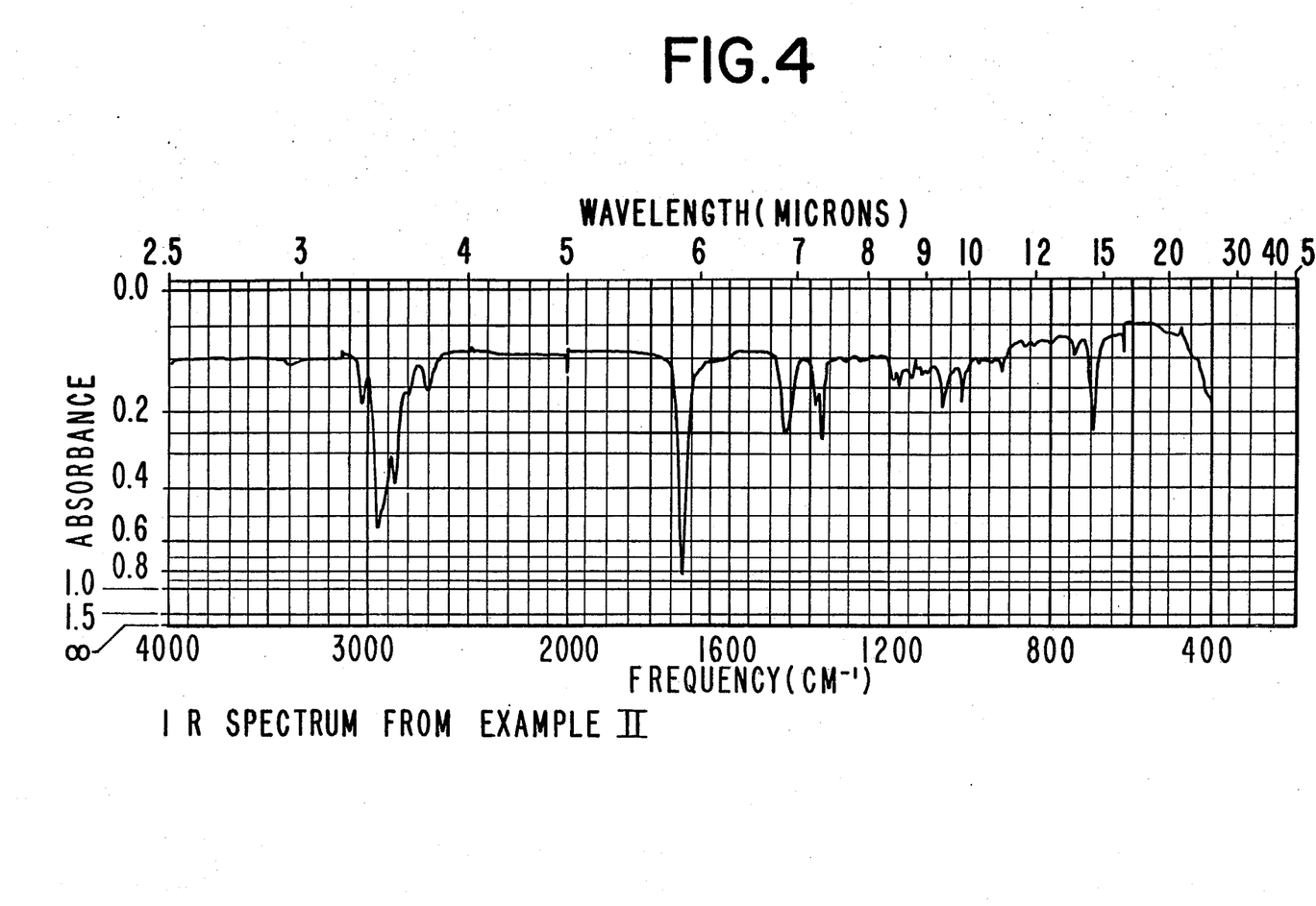
FIG. 4 is the Infrared spectrum of the reaction product produced according to Example II.

In Infrared spectrum is set forth in FIG. 4.

MS Data:

m/e (decreasing intensity): 136, 93, 121, 43, 41, 192 (mol. ion).

IR Data (film):

3030, 2950, 2870, 2795, 2705, 1718, 1410, 1405, 1385, 1370, 1070, 1018, 695 cm$^{-1}$.

NMR Data (100 MHz, CDCl$_3$):

| δ, ppm | Interpretation |
|---|---|
| 9.23 doublet, J=5Hz<br>9.29 doublet, J=5Hz | CHO / H |
| 5.88–6.30 multiplet | H / H |
| 1.22 singlet<br>1.17 singlet | CH$_3$ |
| 0.95 doublet, J=7Hz<br>0.96 doublet, J=7Hz | H—CH$_3$ / CH$_3$ |

EXAMPLE III

PREPARATION OF APLHA, 1(and 4)-DIMETHYL-4(and 1)-ISOPROPYLBICYCLO[2.2.2]OCT-5-ENE-2-METHANOL Reaction:

(wherein X is chloro)

Figure 5:
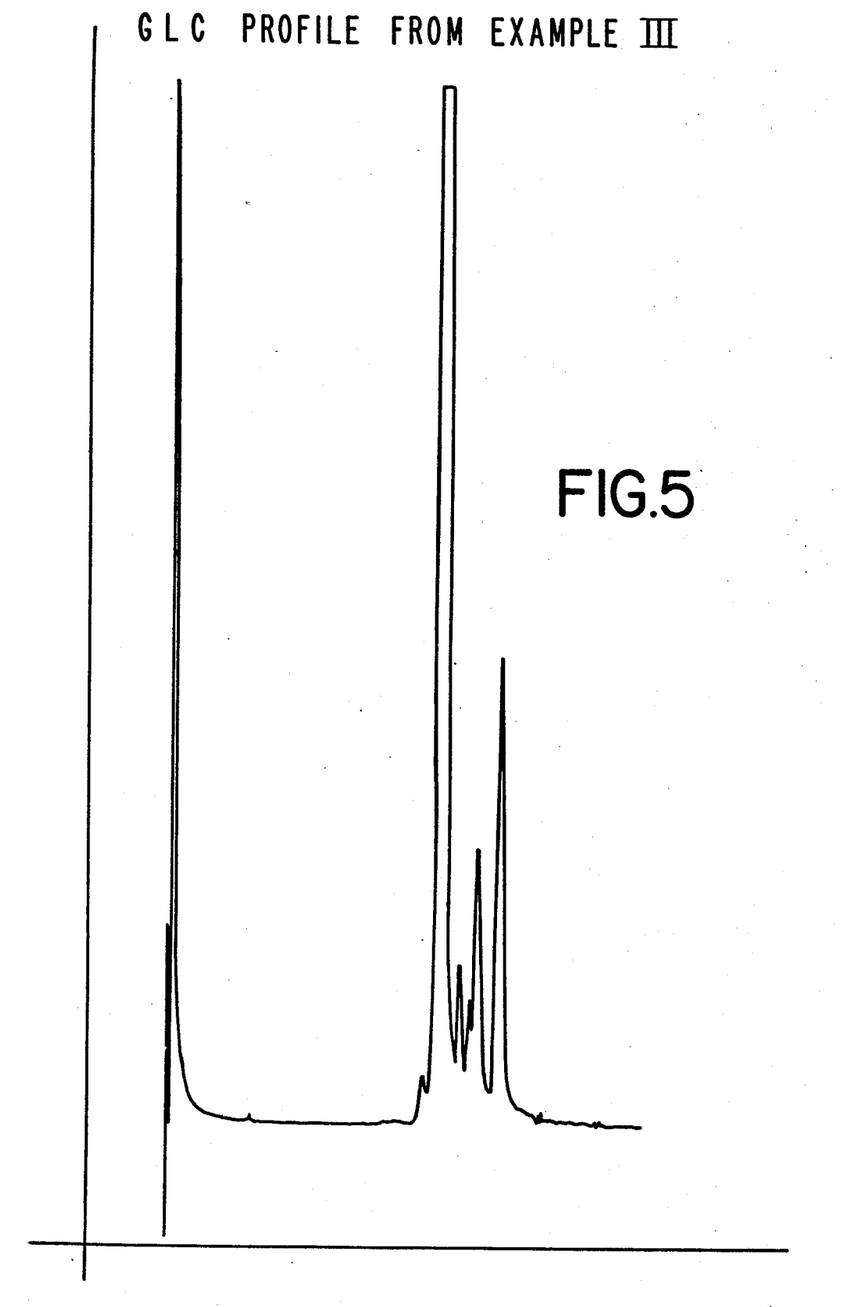
FIG. 5 is the GLC profile of the reaction product produced according to Example III.

A solution of 256 g of 1 (or 4)-isopropyl-4(or 1)-methylbicyclo[2.2.2]oct-5-ene-2-carboxaldehyde (prepared according to Example II) in 167 g of tetrahydrofuran is added in 65 minutes to 436 g of 3 molar methylmagnesium chloride in tetrahydrofuran at reflux (69°-71° C.). The reaction mass is stirred an additional 2 hours at reflux and then is cooled to room temperature. The Grignard complex is decomposed by slow addition of 158 g of saturated ammonium chloride solution, and the resulting magnesium salts are removed by filtration. The filtrate is concentrated under reduced pressure (20-50 mm Hg) to remove the tetrahydrofuran, and the stripped crude product is then distilled quickly through a short column to give 228 g of oil, b.p. 100°-199° C./3 mm Hg. Redistillation through a 12"×1" Goodloe packed column gives 132 g of oil, b.p. 106°-113° C./3 mm Hg, which is shown to be a mixture of isomers having the structures:

The GLC profile for the reaction product is set forth in FIG. 5 (conditions: 10'×⅛"5% K-20M column, programmed at 100°-200° C. at 10° C. per minute).

Figure 6:
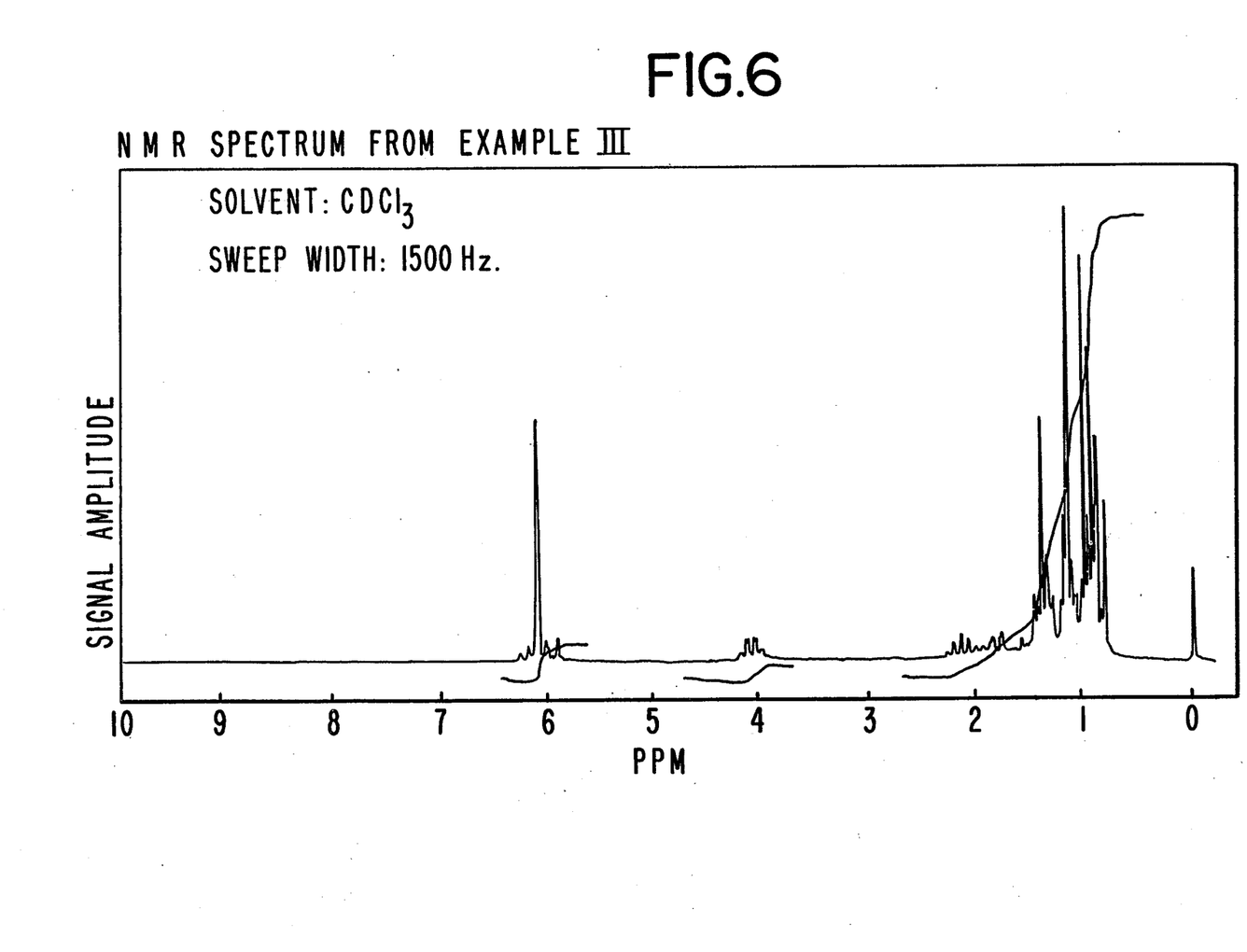
FIG. 6 is the NMR spectrum of the reaction product produced according to Example III.

The NMR spectrum for the final product is set forth in FIG. 6.

Figure 7:
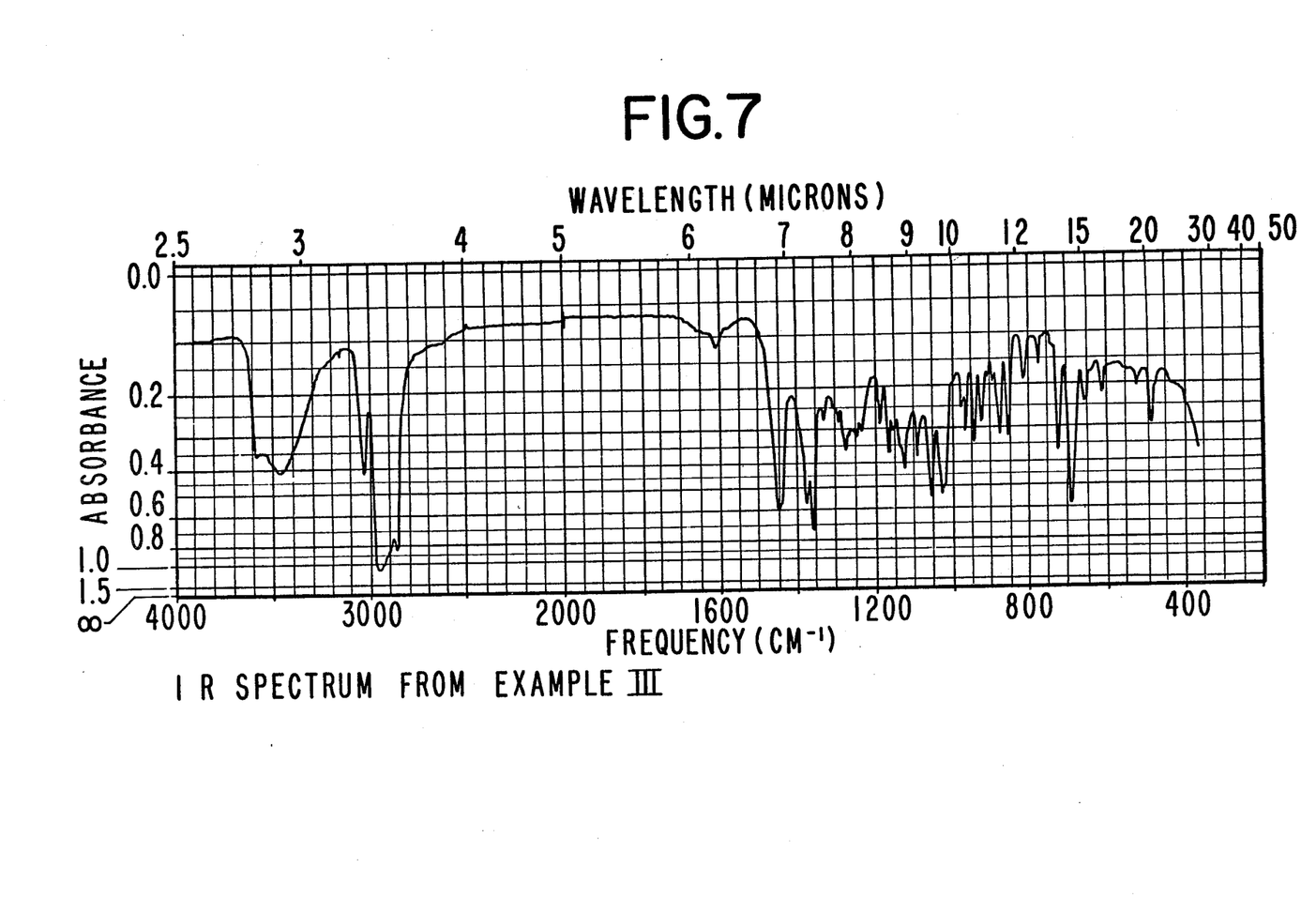
FIG. 7 is the Infrared spectrum of the reaction product produced according to Example III.

The Infrared spectrum for the final product is set forth in FIG. 7.

The Infrared Data (film) is as follows:

3570, 3460, 3010, 2950, 2860, 1610, 1460, 1380, 1365 cm$^{-1}$.

The NMR Data (CDCl$_3$, 100 MHz) is as follows:

| δ, ppm | Interpretation |
|---|---|
| 5.90–6.30 multiplet | \\C=C/ with H's |

-continued

| δ, ppm | Interpretation |
|---|---|
| 3.98–4.28 | H—C(OH)(CH₃) with H |
| 1.17 singlet | CH₃ |
| 1.99 doublet, J=6Hz  1.88 doublet, J=6Hz | (CH₃)₂CH— |

The Mass Spectral Data is as follows:
m/e (decreasing intensity): 136, 121, 43, 93, 41,..., 208(m+).

EXAMPLE IV

ROSE FORMULATION

To demonstrate the use of the bicyclo[2.2.2]octenemethanol derivatives produced according to Example III in a rose formulation, the following formula is provided:

| Ingredient | Parts by Weight |
|---|---|
| Phenylethyl alcohol | 175 |
| Geraniol | 400 |
| Tricholromethylphenyl carbinyl acetate | 20 |
| Phenylethyl acetate | 60 |
| Undecylenic aldehyde (10% in diethyl phthalate) | 5 |
| n-Nonyl aldehyde (10% in diethyl phthalate) | 2 |
| Musk ketone | 10 |
| Musk ambrette | 10 |
| Eugenol phenyl acetate | 20 |
| Citronellol | 100 |
| Vanillin (10% in diethyl phthalate) | 6 |
| Eugenol | 30 |
| Citronellyl formate | 30 |
| Geranyl acetate | 10 |
| Linalool | 40 |
| Geranyl phenyl acetate | 50 |
| Cis beta, gamma-hexenyl acetate | 2 |
| Bicyclo[2.2.2]octenemethanol derivative mixture having the formula:  prepared according to Example III | 25 |
| | 1000 Total |

The addition of 2.5% of bicyclo[2.2.2]octenemethanol derivatives produced according to Example III lends a great deal of strength and character to the rose fragrance. It contributes great floralcy and woodyness with clary-sage and violet leaf nuances to this rose aroma.

At lower concentrations (0.5%) its contribution is more subtle, however, it still gives an interesting natural effect.

This product may normally be used from approximately 0.01% to 10% in perfume compositions. For special effects, however, higher concentrations (50% plus) can be used.

EXAMPLE V

PREPARATION OF A SOAP COMPOSITION

100 Grams of soap chips are mixed with one gram of the perfume composition of Example IV until a substantially homogeneous composition is obtained. The perfumed soap composition manifests an excellent rose character with excellent and very strong sweet, woody and floral notes and clary-sage, violet leaf undertones.

EXAMPLE VI

PREPARATION OF A DETERGENT COMPOSITION

A total of 100 grams of detergent powder (a low phosphate content detergent composition which contains 12% by weight phosphate builder, 8% hardness mineral ion insensitive detergent, 0.9% by weight maleic anhydride-vinyl compound co-polymer and 2% alkylene oxide condensation product prepared according to Example IV at column XI, of U.S. Pat. No. 4,000,080 issued on Dec. 28, 1976) is intimately admixed with 0.15 grams of the perfume composition of Example IV until a substantially homogeneous composition is obtained. This composition has an excellent rose aroma with excellent and very strong sweet, woody and floral notes and clary-sage, violet leaf undertones.

EXAMPLE VII

PREPARATION OF A COSMETIC-POWDER COMPOSITION

A cosmetic powder is prepared by mixing in a ball mill, 100 g of talcum powder with 0.25 g of bicyclo[2.2.-2]octenemethanol derivatives produced according to Example III, having the generic structures:

wherein the wavy lines represent exo and endo configurations. It has an excellent rose, sweet, woody and floral aroma with clary-sage and violet leaf understones.

EXAMPLE VIII

PERFUMED LIQUID DETERGENT

Concentrated liquid detergents with sweet, woody and floral aromas with clary-sage, violet leaf and rose undertones are prepared containing 0.10%, 0.15% and 0.20% of bicyclo[2.2.2]octenemethanol derivatives produced according to Example III, having the generic structures:

They are prepared by adding and homogeneously mixing the appropriate quantity of bicyclo[2.2.2]octenemethanol derivative in a liquid detergent which is a homogeneous single-phase heavy-duty liquid detergent composition containing:
  a. 12.5% by weight based on the free acid form of an anionic detersive surfactant;
  b. 0.5% magnesium sulfate;
  c. 12% by weight of an ethoxylated nonionic detersive surfactant;
  d. 3% by weight of a water-soluble bis(styrylsulfonate)biphenyl brightener; and
  e. the balance of the composition being water,
prepared according to U.S. Pat. No. 3,998,750 issued on Dec. 21, 1976. The detergents all possess a sweet, woody, floral aroma with clary-sage, violet leaf and rose undertones.

EXAMPLE IX

PREPARATION OF A COLOGNE AND HANDKERCHIEF PERFUME

The bicyclo[2.2.2]octenemethanol derivative prepared according to the process of Example III having the structures:

is incorporated in a cologne at a concentration of 2.5% in 85% aqueous ethanol; and into a handkerchief perfume at a concentration of 20% (in 95% aqueous ethanol). Another cologne is prepared at a concentration of 2.0% and yet a third cologne is prepared at a concentration of 3.5%. A distinct and definite sweet, woody, floral aroma with clary-sage, violet leaf and rose undertone is imparted to each of the colognes at each of the concentrations and to the handkerchief perfume.

EXAMPLE X

PREPARATION OF A COLOGNE AND HANDKERCHIEF PERFUME

The composition of Example IV is incorporated in a cologne at concentrations of 2.0%, 2.5%, 3.0%, 3.5% and 4.0% in 85% aqueous ethanol; and into a handkerchief perfume at concentrations of 15%, 20% and 25% (in 95% aqueous ethanol). The use of the bicyclo[2.2.2]octenemethanol derivative prepared according to the process of Example III and the composition of Example IV affords a distinct and definite strong rose aroma with sweet, woody, floral notes and clary-sage and violet leaf undertones to the handerkerchief perfume and cologne.

EXAMPLE XI

PREPARATION OF SOAP COMPOSITION

One hundred grams of soap chips are mixed with one gram of the bicyclo[2.2.2]octenemethanol derivative produced according to Example III havig the generic structures:

until a substantially homogeneous composition is obtained. The perfumed soap composition manifests an excellent sweet, woody, floral aroma with clary-sage, violet leaf and rose undertones.

EXAMPLE XII

PREPARATION OF A DETERGENT COMPOSITION

A total of 100 grams of detergent powder (a low phosphate content detergent composition which contains 12% by weight phosphate builder, 8% hardness mineral ion insensitive detergent, 0.9% by weight maleic anhydride-vinyl compound co-polymer and 2% alkylene oxide condensation product prepared according to Example IV at column XI, of U.S. Pat. No. 4,000,080 issued on Dec. 28, 1976) is intimately admixed with 0.15 grams of the perfume composition of Example IV until a substantially homogeneous composition is obtained. This composition has an excellent rose aroma with excellent and very strong sweet, woody and floral notes and clary-sage, violet leaf undertones.

EXAMPLE XIII

TOBACCO FORMULATION

A tobacco mixture is produced by admixing the following ingredients:

| Ingredient | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco. The following flavor formulation is prepared:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |

| Ingredient | Parts by Weight |
| --- | --- |
| Water | 41.90 |

The above-stated tobacco flavor formulation is applied at the rate of 0.1% to all of the cigarettes produced using the above tobacco formulation. Half of the cigarettes are then treated with 500 or 1,000 ppm of bicyclo[2.2.2]octenemethanol derivative produced according to the process of Example III having the generic structures:

The control cigarettes not containing the bicyclo[2.2.2]octenemethanol derivatives and the experimental cigarettes which contain the bicyclo[2.2.2]octenemethanol derivatives produced according to the process of Example III are evaluated by paired comparison and the results are as follows:

The experimental cigarettes are found, on smoking, to have a sweeter, spicey, woody-oriental, Virginia hay tobacco-like taste with much more body and much more natural tobacco-like aroma prior to smoking and on smoking in the mainstream and in the sidestream.

Furthermore, the tobacco of the experimental cigarettes, prior to smoking, have strong, sweet, spicey and woody-hay tobacco-like notes. All cigarettes are evaluated for smoke flavor with a 20 mm cellulose acetate filter.

Accordingly, it is concluded that the bicyclo[2.2.2]octenemethanol derivatives produced according to the process of Example III having the generic structures:

wherein the wavy lines represent exo and/or endo configurations of the ethanol moiety with respect to the carbon-carbon double bond of the bicyclooctene moiety, enhances the tobacco-like taste and aroma, particularly tobacco/haylike taste of the blended cigarette, imparting to it sweet, spicey and woody-oriental hay tobacco-like nuances.

EXAMPLE XIV

In a vessel associated with a source of heat, a quantity of diced Versamide 930 amounting to 88 parts by weight is heated to about 130° C. at which temperature the resin is a pourable and stirrable body of liquid. A quantity of the perfume formulation of Example IV having a rose bouquet amounting to 12 parts by weight is stirred into the liquid resin until a uniform blend is achieved at which time the mixture is poured into standing cold water to facilitate rapid cooling and solidification and minimize loss of perfume formulation. The product is a clear amber solid having a highly polished surface with a pronounced odor faithfully reproducing the fragrance of the rose perfume formulation used in making it. The material has a "rose character" with excellent and very strong, sweet, woody and floral notes and clary-sage, violet leaf undertones. The resulting product is in the form of a solid solution which blends itself to molding under heat and pressure into objects of jewelry such as pendant earrings, to casting in molds to form decorative art objects, and to spreading as a film on substrates such as Christmas tree ornaments, glass light bulbs, and the like.

What is claimed is:

1. An organometallic compound having the structure:

wherein X is selected from the group consisting of chloro, bromo and iodo and wherein the wavy lines represent exo or endo configurations of the bicyclooctene nucleus with respect to the organometallic oxyethane moiety.

2. An organometallic compound having the structure:

wherein X is selected from the group consisting of chloro, bromo and iodo and wherein the wavy lines represent exo or endo configurations of the bicyclooctene nucleus with respect to the organometallic oxyethane moiety.

3. A mixture of organometallic compounds having the structures:

wherein X is selected from the group consisting of chloro, bromo and iodo and wherein the wavy lines represent exo or endo configurations of the bicyclooctene nucleus with respect to the organometallic oxyethane moiety.

* * * * *